(12) United States Patent
Day et al.

(10) Patent No.: US 9,456,890 B2
(45) Date of Patent: Oct. 4, 2016

(54) SCAFFOLD FOR BONE AND TISSUE REPAIR IN MAMMALS

(71) Applicant: The Curators of the University of Missouri, Columbia, MO (US)

(72) Inventors: Delbert E. Day, Rolla, MO (US); Steven B. Jung, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 366 days.

(21) Appl. No.: 13/740,365

(22) Filed: Jan. 14, 2013

(65) Prior Publication Data

US 2013/0144400 A1 Jun. 6, 2013

Related U.S. Application Data

(63) Continuation-in-part of application No. 12/354,313, filed on Jan. 15, 2009, now Pat. No. 8,353,966.

(51) Int. Cl.
| | | |
|---|---|---|
| *A61F 2/02* | (2006.01) | |
| *A61L 27/10* | (2006.01) | |
| *A61L 27/56* | (2006.01) | |
| *A61L 27/44* | (2006.01) | |
| *A61L 27/50* | (2006.01) | |
| *A61L 27/60* | (2006.01) | |
| *A61F 2/30* | (2006.01) | |

(52) U.S. Cl.
CPC .................. *A61F 2/02* (2013.01); *A61L 27/10* (2013.01); *A61L 27/446* (2013.01); *A61L 27/50* (2013.01); *A61L 27/56* (2013.01); *A61L 27/60* (2013.01); *A61F 2/30965* (2013.01); *A61F 2002/3092* (2013.01); *A61F 2002/30448* (2013.01); *A61F 2002/30766* (2013.01); *A61F 2220/005* (2013.01); *A61L 2430/02* (2013.01); *A61L 2430/30* (2013.01); *A61L 2430/34* (2013.01)

(58) Field of Classification Search
CPC .......... A61F 2/02; A61F 2002/30766; A61F 2002/30448; A61F 2220/005; A61F 2/30965; A61F 2002/3092; A61L 27/446; A61L 27/10; A61L 27/56; A61L 27/50; A61L 27/60; A61L 2430/34; A61L 2430/02; A61L 2430/30; C08L 67/04; C08L 33/12
See application file for complete search history.

(56) References Cited

U.S. PATENT DOCUMENTS

| | | | |
|---|---|---|---|
| 3,906,550 A | | 9/1975 | Rostoker et al. |
| 4,512,038 A | | 4/1985 | Alexander et al. |
| 5,039,566 A | * | 8/1991 | Skubic et al. ................ 428/113 |
| 5,053,035 A | | 10/1991 | McLaren |
| 5,062,798 A | * | 11/1991 | Tsuge et al. ............... 433/201.1 |
| 5,176,708 A | * | 1/1993 | Frey et al. .................... 623/13.2 |
| 5,263,984 A | * | 11/1993 | Li et al. ..................... 623/13.18 |
| 5,312,669 A | | 5/1994 | Bedard |
| 5,344,456 A | * | 9/1994 | Nonami et al. ............ 623/23.72 |
| 5,624,674 A | * | 4/1997 | Seare, Jr. ....................... 424/400 |
| 5,876,452 A | * | 3/1999 | Athanasiou et al. ...... 623/23.72 |

(Continued)

FOREIGN PATENT DOCUMENTS

EP 0469070 B1 9/1996

*Primary Examiner* — Gregory Anderson
*Assistant Examiner* — Son Dang
(74) *Attorney, Agent, or Firm* — Senniger Powers LLP

(57) ABSTRACT

A mammalian tissue scaffold and method for making a tissue scaffold including a rigid scaffold body of biocompatible glass fibers bonded together and in special alignment to define open channels within the scaffold to allow fluid flow into and within the scaffold.

26 Claims, 17 Drawing Sheets

(56) References Cited

U.S. PATENT DOCUMENTS

| | | | | |
|---|---|---|---|---|
| 6,113,640 | A * | 9/2000 | Tormala et al. | 623/18.11 |
| 6,260,388 | B1 * | 7/2001 | Borrelli et al. | 65/393 |
| 6,333,029 | B1 * | 12/2001 | Vyakarnam et al. | 424/93.1 |
| 6,358,531 | B1 | 3/2002 | Day et al. | |
| 6,379,648 | B1 | 4/2002 | Day et al. | |
| 6,399,215 | B1 * | 6/2002 | Zhu et al. | 428/544 |
| 6,514,515 | B1 * | 2/2003 | Williams | A61L 27/18 424/424 |
| 6,692,761 | B2 | 2/2004 | Mahmood et al. | |
| 6,709,744 | B1 | 3/2004 | Day et al. | |
| 6,993,406 | B1 * | 1/2006 | Cesarano et al. | 700/119 |
| 7,022,522 | B2 | 4/2006 | Guan et al. | |
| 7,201,917 | B2 | 4/2007 | Malaviya et al. | |
| 7,299,805 | B2 | 11/2007 | Bonutti | |
| 7,338,517 | B2 | 3/2008 | Yost et al. | |
| 7,435,594 | B2 | 10/2008 | Gong et al. | |
| 7,449,180 | B2 | 11/2008 | Kisiday et al. | |
| 7,458,991 | B2 | 12/2008 | Wang et al. | |
| 7,524,335 | B2 * | 4/2009 | Slivka et al. | 623/23.75 |
| 7,947,069 | B2 * | 5/2011 | Sanders | 623/1.1 |
| 2002/0160175 | A1 | 10/2002 | Pirhonen | |
| 2003/0078653 | A1 * | 4/2003 | Vesely et al. | 623/2.16 |
| 2003/0097180 | A1 | 5/2003 | Tormala et al. | 623/13.18 |
| 2003/0105530 | A1 * | 6/2003 | Pirhonen et al. | 623/23.72 |
| 2004/0170692 | A1 | 9/2004 | Day et al. | |
| 2004/0267362 | A1 | 12/2004 | Hwang et al. | |
| 2005/0118236 | A1 * | 6/2005 | Qiu et al. | 424/443 |
| 2007/0243991 | A1 | 10/2007 | Brow et al. | |
| 2007/0244484 | A1 * | 10/2007 | Luginbuehl | 606/86 |
| 2007/0276509 | A1 | 11/2007 | Ratcliffe et al. | |
| 2007/0282455 | A1 * | 12/2007 | Luginbuehl et al. | 623/23.72 |
| 2008/0077251 | A1 * | 3/2008 | Chen et al. | 623/23.72 |
| 2008/0208358 | A1 | 8/2008 | Bellamkonda et al. | |
| 2009/0024229 | A1 * | 1/2009 | Chen et al. | 623/23.73 |
| 2010/0063599 | A1 * | 3/2010 | Brunelle et al. | 623/23.72 |
| 2010/0121463 | A1 | 5/2010 | Tormala et al. | |

* cited by examiner

SCAFFOLD FOR BONE AND TISSUE REPAIR IN MAMMALS

This is a continuation-in-part application based on U.S. application Ser. No. 12/354,313 filed Jan. 15, 2009, issued Jan. 15, 2013 as U.S. Pat. No. 8,353,966, the entire disclosure of which is incorporated by reference.

FIELD OF THE INVENTION

This invention relates to a biocompatible scaffold for implantation into mammals to facilitate bone and tissue repair, regeneration, and proliferation.

BACKGROUND OF THE INVENTION

The use of tissue scaffold to facilitate the repair and regrowth of bone and other tissue is known in the art, for example, from U.S. Pat. No. 7,338,517 which discloses an implantable scaffold with biopolymer fibrils aligned in helical patterns of opposite directions.

U.S. Pat. No. 7,416,564 describes a bone scaffold made from porous ceramic substrate of a material such as zirconia which is then coated with a fluorapatite layer and a hydroxyapatite layer. The porous substrate was prepared by dipping a foam template into a slurry. The porosity is aligned irregularly and randomly and does not run continuously along a longitudinal axis from one end of the object to the other end. The fabrication requires repeated dipping and drying.

SUMMARY OF THE INVENTION

Briefly, therefore, the invention is directed to a tissue scaffold comprising a rigid scaffold body having a scaffold central axis, a scaffold transverse dimension, and a scaffold lengthwise dimension which is greater than the scaffold transverse dimension, the scaffold body having a compressive strength between about 20 and about 250 MPa and comprising biocompatible inorganic glass fibers each having a fiber transverse dimension and a fiber lengthwise dimension which is at least about 10 times the fiber transverse dimension; wherein each of the fibers has a diameter between about 20 and about 5000 microns; wherein the fibers are bonded together; and wherein at least about 75 vol % of the fibers extend generally in the direction of the scaffold central axis, are generally free of helical orientation about the scaffold central axis, and are arranged to define open channels within the scaffold which allow fluid flow into and lengthwise within the scaffold.

In another aspect the invention is directed to a tissue scaffold comprising a rigid scaffold body having a central axis, a scaffold transverse dimension, and a scaffold lengthwise dimension which is greater than the scaffold transverse dimension, the scaffold body having a compressive strength between about 20 and about 250 MPa and comprising: biocompatible inorganic glass fibers each having a fiber transverse dimension and a fiber lengthwise dimension which is at least about 10 times the fiber transverse dimension; wherein the fibers are bonded together; wherein each of the fibers has a diameter between about 20 and about 5000 microns; and wherein at least about 75 vol % of the fibers extend generally parallel to the scaffold central axis, and are arranged to define open channels within the scaffold which allow fluid flow into and lengthwise within the scaffold.

The invention is also directed to a tissue scaffold comprising a scaffold body having a central axis, a scaffold transverse dimension, and a scaffold lengthwise dimension which is greater than the scaffold transverse dimension, the scaffold body comprising: biocompatible inorganic glass fibers each having a fiber transverse dimension and a fiber lengthwise dimension which is at least about 10 times the fiber transverse dimension; wherein each of the fibers has a diameter between about 20 and about 5000 microns; wherein the fibers are bonded together; wherein at least about 75 vol % of the fibers extend generally in the direction of the scaffold central axis, and are arranged to define open channels lengthwise through a core within the scaffold, which channels allow fluid flow into and lengthwise within the scaffold.

In another aspect the invention is directed to a method for making a tissue scaffold comprising: heating inorganic biocompatible glass fibers in a mold to a temperature where the fibers partially fuse to each other to form a rigid scaffold body having a scaffold central axis, a scaffold transverse dimension, and a scaffold lengthwise dimension which is greater than the scaffold transverse dimension, the scaffold body having, a compressive strength between about 20 and about 250 MPa; wherein the biocompatible glass fibers each has a fiber transverse dimension and a fiber lengthwise dimension which is at least about 10 times the fiber transverse dimension; wherein the fibers have a diameter between about 20 and about 5000 microns; and wherein at least about 75 vol % of the fibers extend generally in the direction of the scaffold central axis, are generally free of helical orientation about the scaffold central axis, and are arranged to define open channels within the scaffold which allow fluid flow into and lengthwise within the scaffold.

Other objects and features of the invention are in part apparent and in part pointed out hereinafter.

DESCRIPTION OF PREFERRED EMBODIMENTS

The tissue scaffold of the present invention is prepared from fibers which are aligned so that a majority of the fibers are substantially aligned in a parallel direction. The scaffold is prepared by placing and orienting fibers in a unidirectional manner in a mold. The fibers in the mold are heated to a temperature where the fibers soften and bond together. In one preferred embodiment, the fibers are self bonded in the sense that no adhesive, braze, or other external bonding agent is used for bonding. An alternative embodiment employs a biocompatible agent or adhesive to facilitate bonding, such that the fibers are not self bonded, at least in part. Upon cooling, the assemblage of bonded fibers is sufficiently rigid and strong that the assemblage can be removed from the mold and handled. The scaffold is sufficiently rigid that it can be implanted into a mammal where it facilitates the repair and regeneration of hard tissue such as bone (including cortical and cancellous) or soft tissue such as muscle, cartilage, skin, organ, or other hard or soft tissue.

The orientation of the fibers in a lengthwise direction in the self bonded scaffold provides lengthwise channels (or connected pores) among the fibers, which channels provide for uptake into the scaffold of stem cells, growth factors, medicines, red blood cells and other bodily fluids and components carried in bodily fluids. The fibers are arranged to define channels within the scaffold which facilitate fluid flow into and lengthwise within the scaffold from one end to the other end. The orientation also provides for channels in a transverse direction generally perpendicular to the lengthwise direction of the oriented fibers, to facilitate uptake of fluids from the outer surface of the interior or core of the scaffold. These longitudinal and transverse channels exert significant capillary forces on a liquid which cause the liquid to be drawn into the scaffold. This capillary action facilitates the distribution of these fluids and components relatively uniformly through the scaffold and enables fluids to flow from one end of the scaffold to the other or to enter the scaffold from its surface and transmit the liquid to its ends.

Figure 1A:
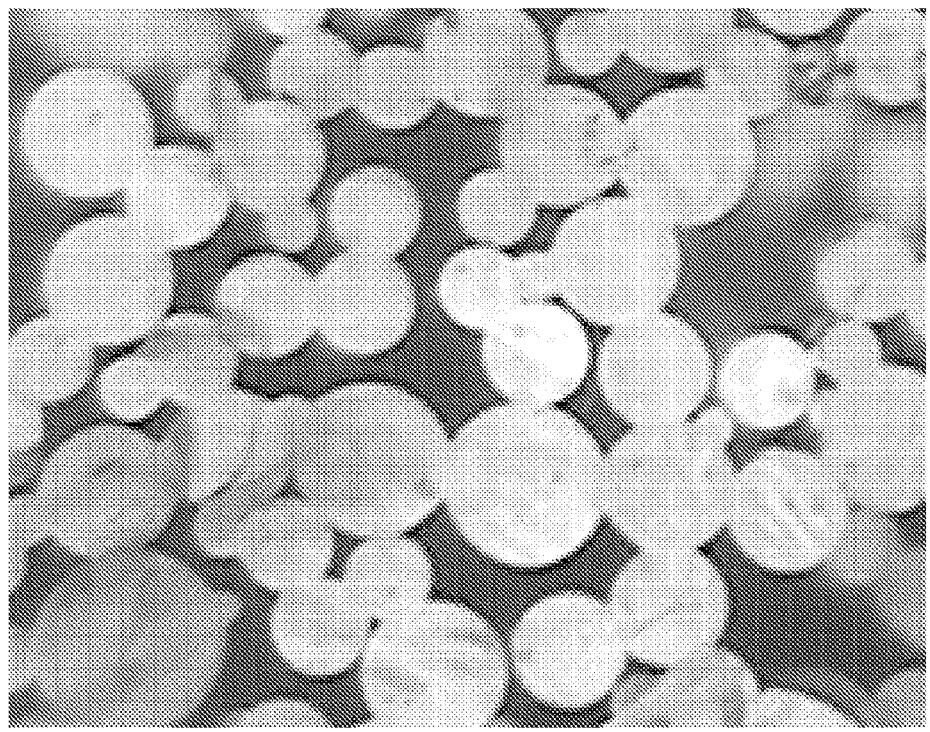
FIG. 1A is an optical micrograph of a transverse cross section of a scaffold of the invention formed by heating fibers at 700° C. for a relatively shorter time than with the scaffold in FIGS. 1B and 1C.
Figure 1B:
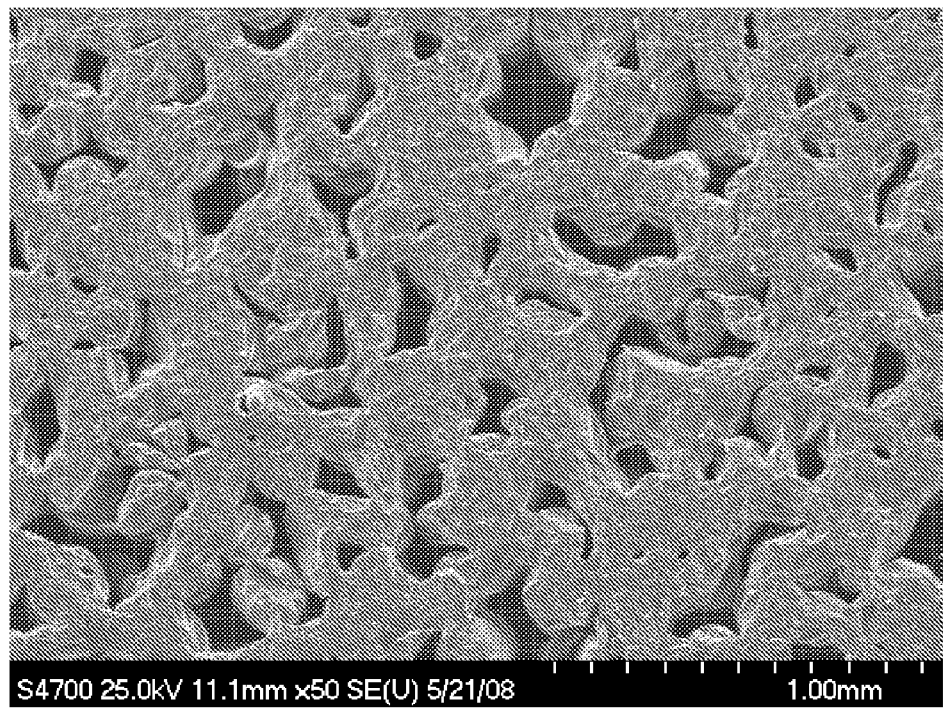
FIGS. 1B and 1C are SEM photographs of a transverse cross section of the scaffold of the invention formed by heating fibers at 700° C. for a relatively longer time than with the scaffold in FIG. 1A.
Figure 1C:
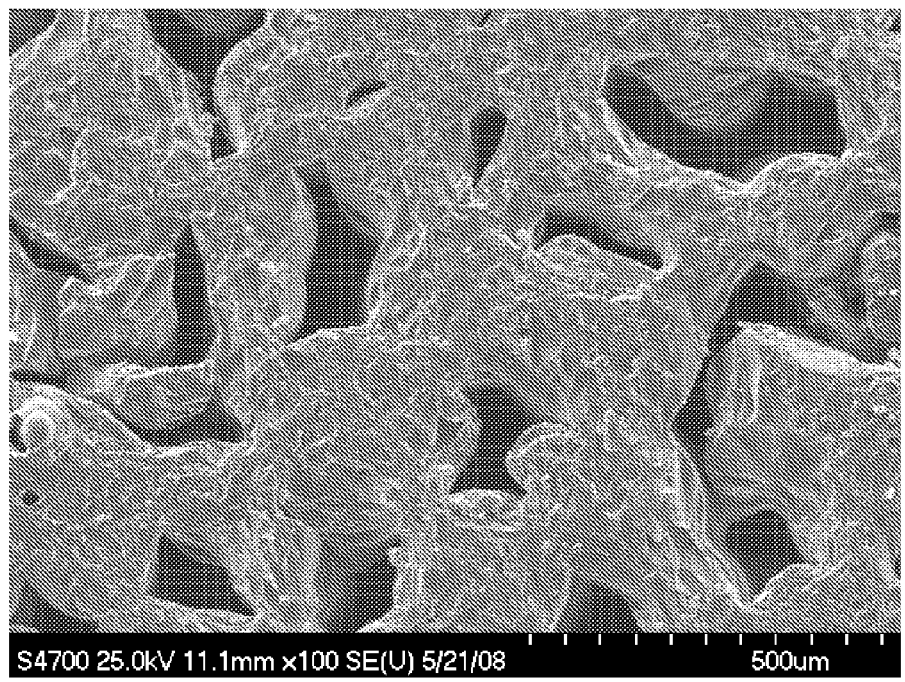

The invention in one embodiment employs fibers having a diameter, prior to molding and softening, between about 20 and about 5000 microns, such as between about 50 and about 5000 microns. In one embodiment the scaffold is prepared from fibers having diameters between about 100 and about 450 microns, such as between about 100 and about 300 microns. In an alternative embodiment, the scaffold is prepared from fibers having diameters up to about 3000 or 5000 microns (3 to 5 mm), which can be deemed more akin to rods than fibers in some contexts, but for purposes of the discussion of this invention fall within the definition of "fibers." FIG. 1A is an optical micrograph of a cross section of a scaffold of the invention showing the self-bonded fibers and pores after heating the fibers at 700° C. for 15 minutes. FIGS. 1B and 1C, which are SEM photographs of a transverse cross section of a different scaffold of the invention having undergone a greater degree of softening and bonding than the scaffold of FIG. 1A, show that after molding and joining to a greater degree (heating at 700° C. for 45 minutes), the transverse cross section of each fiber is no longer precisely circular as it is in a freshly formed fiber. Rather, the softening of the fibers and fusing of adjacent fibers to each other imparts an irregular and irregularly rounded shape to the fibers in transverse cross section. The transverse cross sections here reflect joined fiber cross sections ranging in width—loosely, diameter—from about 50 to about 300 microns.

Figure 2:
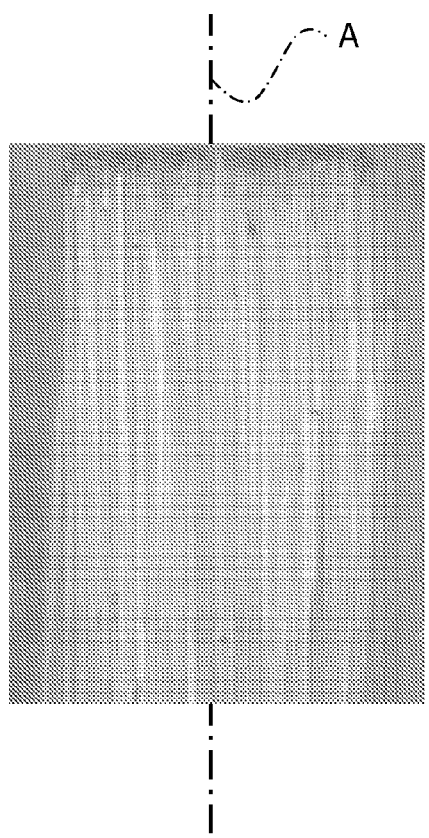
FIG. 2 is a photograph of a lengthwise cross section of the scaffold of the invention showing lengthwise and parallel alignment of fibers.
Figure 7A:
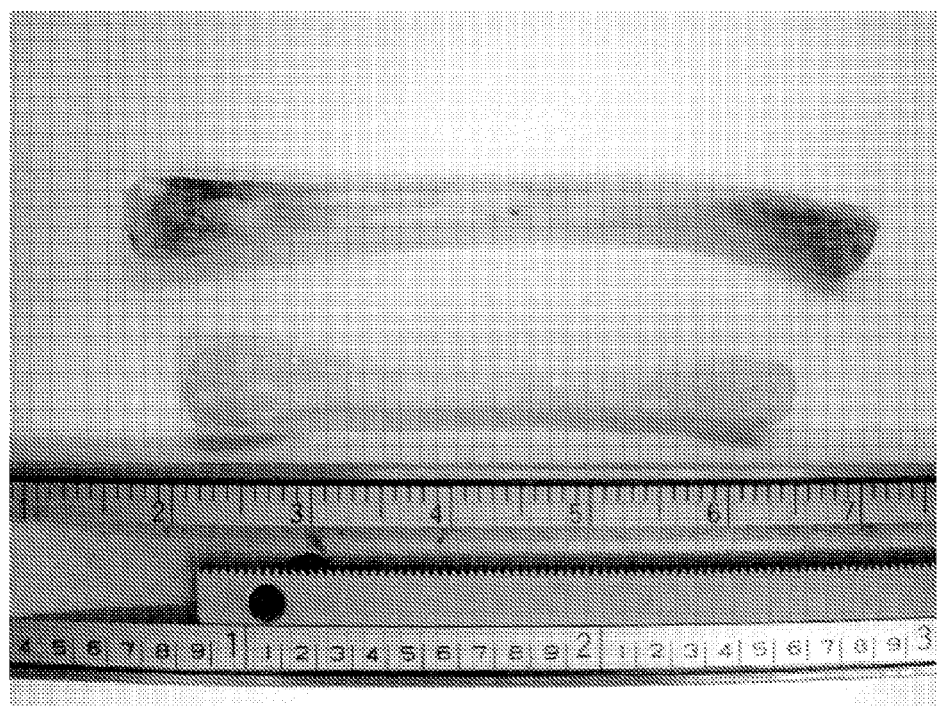
FIGS. 7A and 7B are photographs of a scaffold of the invention next to a chicken bone.
Figure 7B:
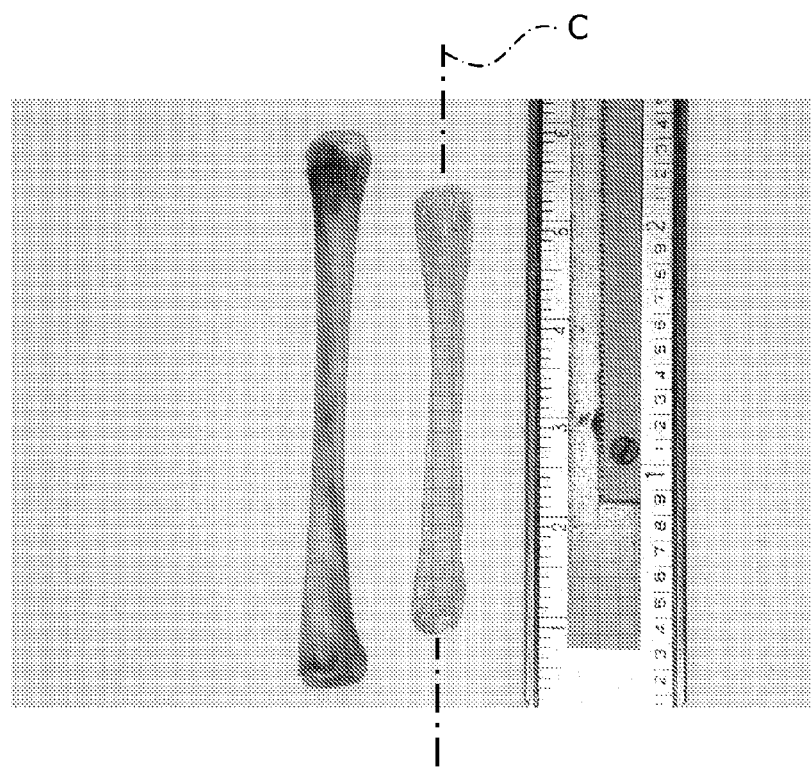
Figure 8A:
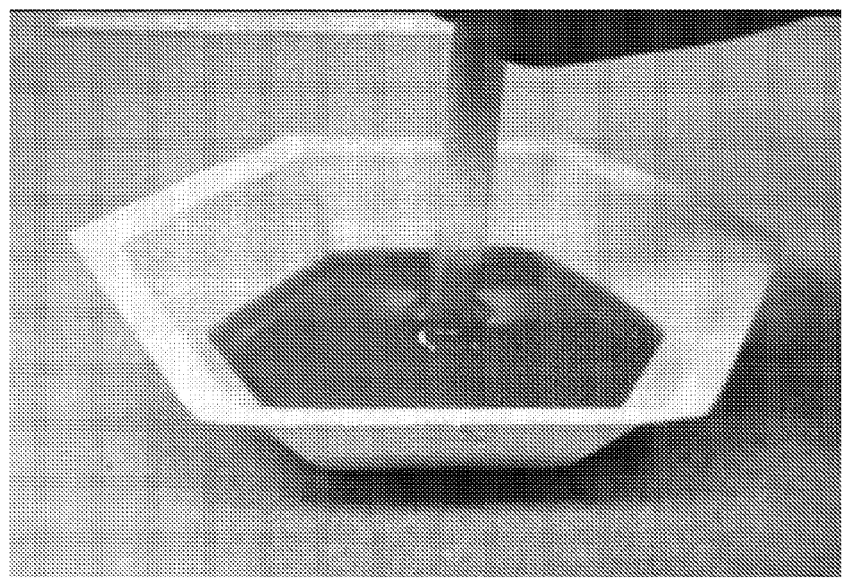
FIGS. 8A, 8B, 8C, 8D, 9A, 9B, 9C, and 9D are still frames extracted from videos taken of experiments described in the working examples.
Figure 8B:
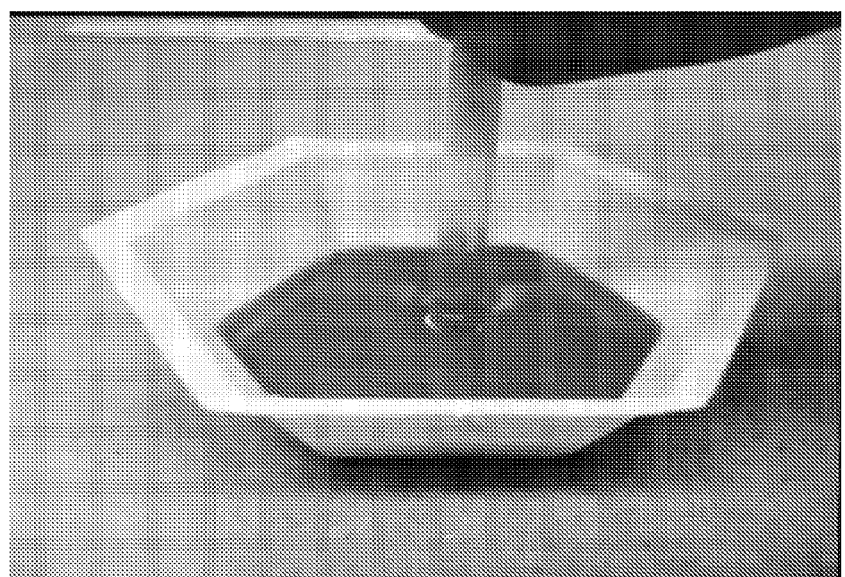
Figure 8C:
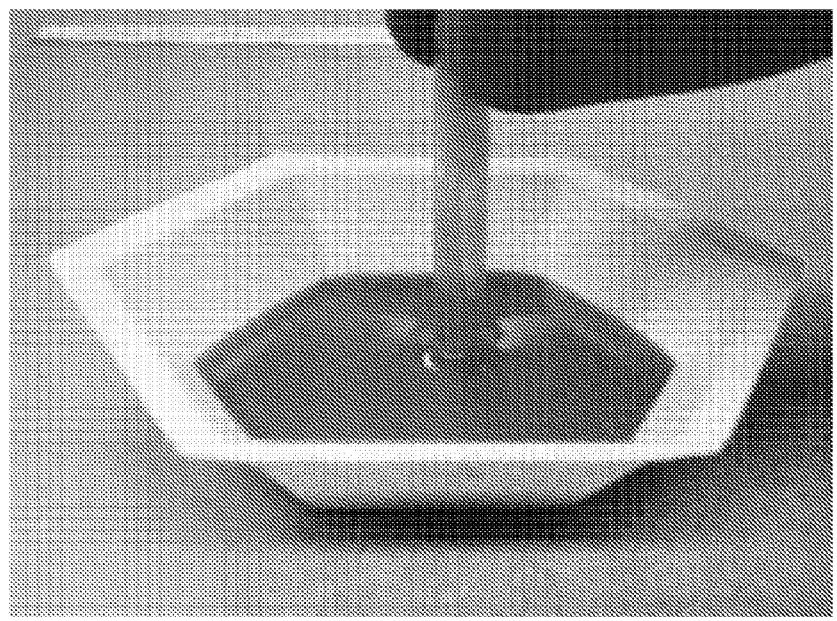
Figure 8D:
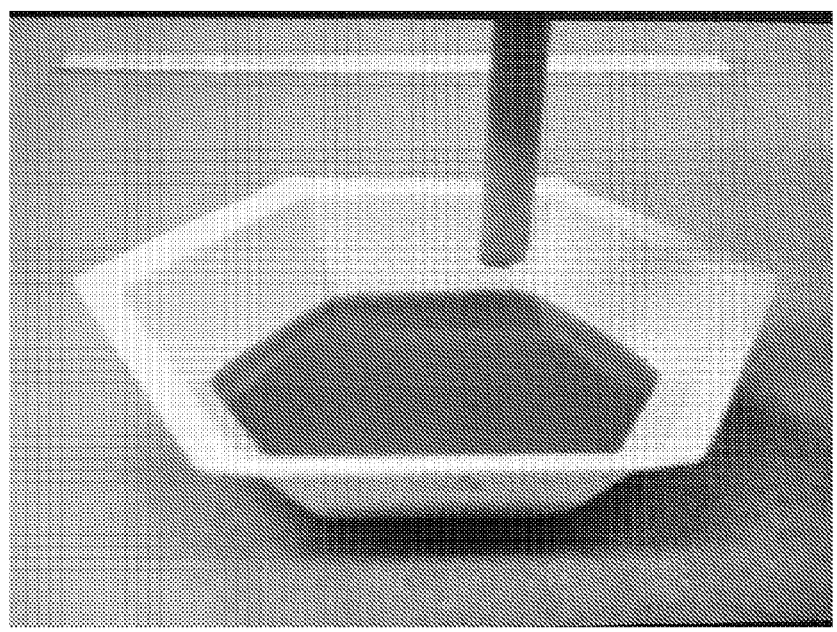
Figure 9A:
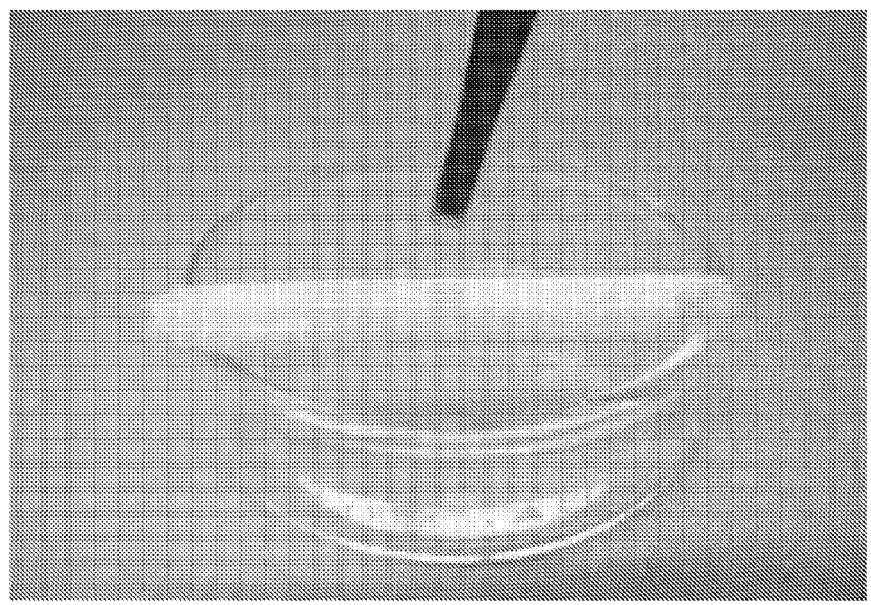
Figure 9B:
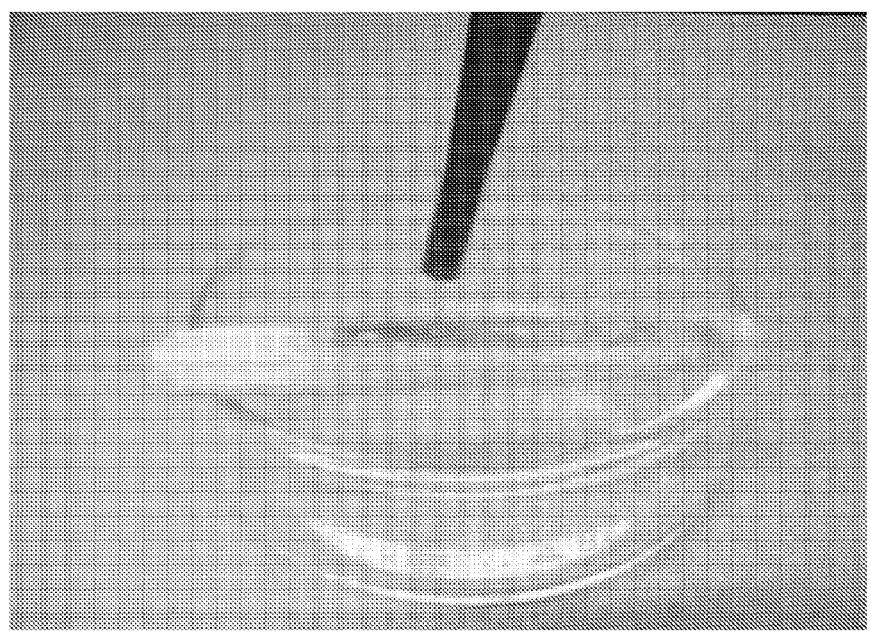
Figure 9C:
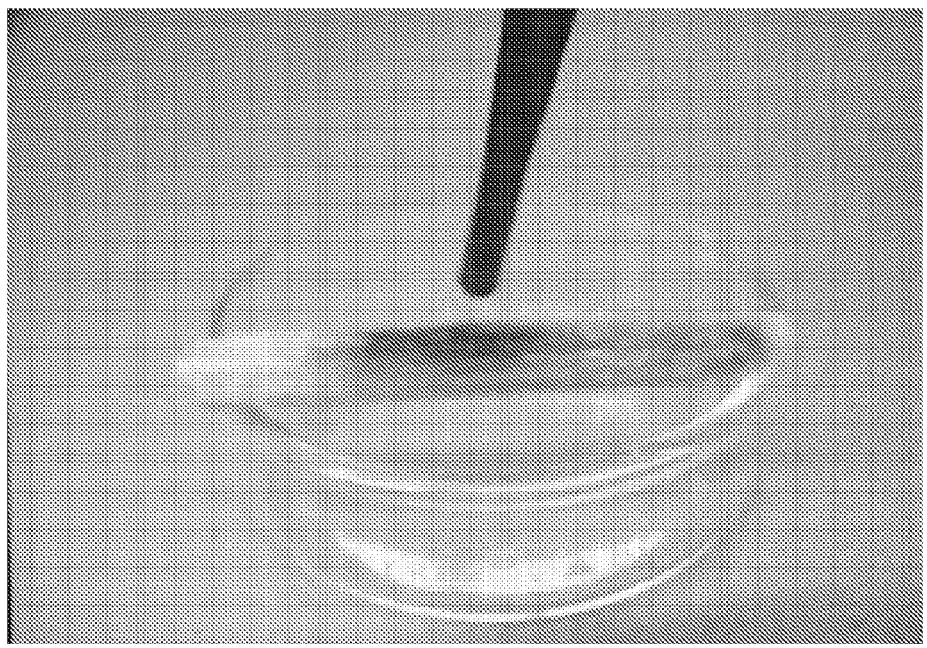
Figure 9D:
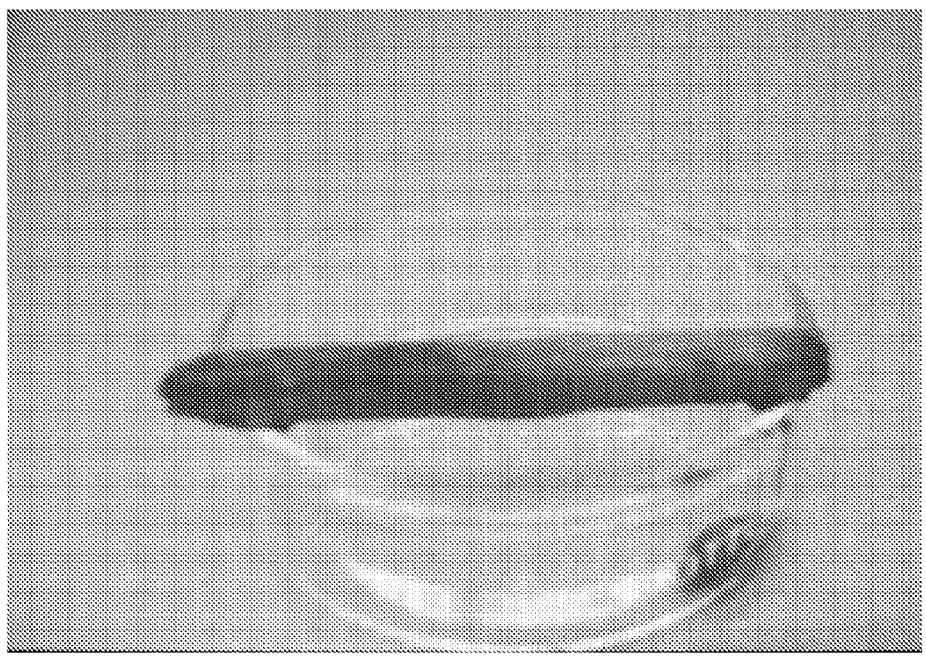

The fibers in the scaffold are bonded together and therefore are not loose fibers; but they retain their identities as separate fibers as shown in FIG. 2, which is a photograph of a longitudinal cross section of a scaffold (heated at 700° C.) of the invention. In one aspect of the invention, at least about 75 or 85% by volume of the fibers in the scaffold are longitudinally co-aligned. In this regard the fibers are co-aligned longitudinally, where "co-aligned longitudinally" and the like phrases (e.g., "in lengthwise co-alignment") as applied to a group of adjacent, bundled, or joined fibers in this application means that the alignment of each fiber in the group at any one place along at least about 75% of its length does not deviate more than about 25 degrees from parallel to the central axis of the scaffold. In one preferred embodiment, each fiber in the group at any one place along at least about 75% of its length does not deviate more than about 15 degrees from parallel to the central axis of the scaffold. In another preferred embodiment, each fiber in the group at any one place along at least about 75% of its length does not deviate more than about 10 degrees from the central axis of the scaffold. So it is evident that this co-alignment aspect does not require 100% precise co-alignment of all fibers. The longitudinal co-alignment aspect also allows for some minor deviation of specific segments of individual fibers to an orientation outside these 25, 15, and 10 degree requirements. This is reflected in the requirement that the longitudinal co-alignment is of each fiber along at least 75% of its length, rather than necessarily along its entire length. So up to about 25% of the length of an individual fiber may be misaligned because, for example, it was bent during the scaffold-making process or otherwise. It can be seen therefore in FIG. 2 that each fiber in the scaffold is not absolutely straight, nor is it lying along an absolutely straight line strictly parallel to all other fibers in the scaffold. And each fiber is oriented generally in the same direction, but each is not oriented in exactly the same direction. Moreover, the scaffold itself in certain embodiments is curved, bent, or otherwise not straight, in which cases the central axis of the scaffold to which the alignment of the fibers is within 25 degrees of parallel is also curved, bent, or otherwise not straight. It will also be evident that in certain embodiments a straight or curved scaffold will be machined into a more complex shape as in FIGS. 7A and 7B, in which instance the scaffold central axis refers to the central axis as molded and prior to machining.

In order to allow capillary action and channel-forming, the scaffold theoretically contains at least three fibers, although from FIG. 2 it can be seen that the scaffold typically comprises dozens and even hundreds of fibers. It can also be seen that the fibers lie generally lengthwise of the scaffold central axis A (i.e., lie generally in the direction of the central axis) and are generally free of helical orientation about the scaffold central axis. This arrangement applies to at least about 75 vol % of the fibers and preferably to substantially all of the fibers. The fibers shown here extend generally parallel to the scaffold central axis A, which is also illustrated as axis B in FIG. 3C, and axis C in FIG. 7B. This embodiment also manifests an optional feature that at least about 75 vol % of the fibers occupies the entire length of the scaffold; but in other embodiments this is not the case.

The requirement of the invention that the fibers are co-aligned longitudinally contemplates that the fibers are positioned so that they have a similar alignment, which similar alignment may be straight, bent, or curved. In a separate and distinct aspect of certain preferred embodiments, this common alignment is limited to a generally straight alignment along at least about 75%, 85%, or 95% of the length of the fibers. In other words, at least about 75%, 85%, or 95% of each fiber is generally straight, i.e., at least about 75%, 85%, or 95% of the length of each fiber has an alignment which is within 10 degrees of a mean straight central axis for the fiber. So up to 5%, 15%, or 25% of the length of each fiber may be curved, bent, or otherwise deviate more than 10 degrees from straight in relation to the overall fiber length, but the rest of each fiber is generally straight in that it so deviates less than 10 degrees. In one preferred embodiment, substantially the entire length of each fiber is generally straight in that it deviates less than 10 degrees from the fiber's average central axis. The "mean straight central axis" is the imaginary central axis for the fiber which is absolutely straight and is an average of all axes along the fiber length.

The fibers in the scaffold are selected to have characteristics suitable for the specific application. In one embodiment, the fibers have a length between about 6 mm and about 15 cm, such as between about 12 mm and about 10 cm or between about 25 mm and about 75 mm. Each fiber has a length which is at least about 10 times its diameter. "Diameter" as used herein refers to the fibers largest dimension transverse to its length, and it does not imply that the fibers are perfectly circular in cross section. Each fiber therefore has a fiber lengthwise dimension which is at least about 10 times the fiber transverse dimension, e.g., diameter. In one embodiment, the fiber length is selected so that all, substantially all, or at least about 85 vol % of the individual fibers extend the entire length of the scaffold. The fibers may be selected to have a pre-molding, pre-joining length which corresponds to the length of the scaffold. Or in most embodiments, the length of the fibers is longer than the desired ultimate scaffold length, and the scaffold is cut to the desired length after molding and joining. In an alternative embodiment, the length of a substantial portion (e.g., at least 40 vol %) or all of the fibers is significantly less than the entire length of the scaffold.

FIGS. 1A, 1B, 1C, 4A and 4B also demonstrate the open and interconnected porosity of the scaffold of the invention. The scaffold is manufactured to have a sufficiently high open and interconnected porosity from end to end of the scaffold to facilitate capillary flow of fluids such as bodily fluids and medicines and components they carry through the length of the scaffold, as well as generally transverse from outside walls of the scaffold into the scaffold interior in directions generally transverse to the longitudinal dimension of the fibers. And the scaffold is manufactured so that the ultimate porosity is low enough that the scaffold has required strength for handling, implantation, and service after implantation. If the porosity is too high, the scaffold risks breakage in service, depending on where it is implanted and the loads it encounters. In a preferred embodiment, the porosity as measured in volume is between about 10% and about 35%, for example between about 10% and about 30%, or between about 10% and about 25%. The porosity is controllable mainly by controlling the degree of softening of the fibers, in that highly softened fibers fuse together more completely to a structure with lower porosity. The degree of softening and fusing is controlled by controlling the joining temperature and time. Porosity is also affected by the fiber diameter and by the range in fiber diameter within a given scaffold. Porosity tends to increase with an increasing range in fiber diameter.

The scaffold of the invention in certain preferred embodiments for use in bone repair has a compressive strength between about 20 and about 250 MPa, for example between about 20 and about 180 MPa or between about 80 and about 140 MPa.

The fibers used in many embodiments of the invention are glass where glass is defined as being at least 99 wt % an amorphous or non-crystalline solid, for example made by fusing a mixture of oxides such as $SiO_2$, $B_2O_3$, $P_2O_5$ (known as glass forming oxides) with basic oxides such as the alkali and alkaline earth oxides. In an alternative embodiment, the fibers include glass ceramics fibers that contain both glassy and crystalline regions which in many respects function in the same manner as a fiber that is completely (100%) non-crystalline. It is acceptable in some applications if the glass fiber crystallizes during the bonding step. The fibers may alternatively be pre-reacted bioactive glasses such as glass fibers pre-reacted to have a thin surface layer of hydroxyapatite. These foregoing different types of fibers are within a common group which are referred to herein as "glass fibers." In a further alternative, the unidirectional scaffold comprises crystalline fibers (such as titanium wires) that would also provide a high amount of capillary action. Alternatively, the scaffold comprises a mix of different types of fibers selected from among these.

The fibers are preferably made from a material which is inorganic and which is biocompatible in that the fibers do not have adverse effects when implanted into mammals. Biocompatible materials include both bioactive and bioinert materials. In certain preferred embodiments, the fibers are also of a bioactive glass in that they are of a glass material which reacts with phosphorus such as phosphorus in bodily fluids to form hydroxyapatite. Bioactive glasses are known in the art, for example, from U.S. Pat. No. 6,054,400; the entire disclosure of which is incorporated herein by reference. Bioactive glasses are available, for example, from Mo-Sci Corporation of Rolla, Mo. In other embodiments, some or all of the fibers may be bioinert rather than bioactive, such as 100% bioinert fibers or a roughly 50/50 mix of bioinert and bioactive fibers.

In general, bioactive glass is one which contains calcium and, when placed in contact with natural body fluids or simulated body fluids, forms a biocompatible calcium phosphate compound such as hydroxyapatite. When such a glass is immersed in or otherwise contacted with natural or simulated body fluids which contain phosphate ions such as in a mammal, the glass dissolves, thereby releasing $Ca^{2+}$ ions into the solution. In this solution, $Ca^{2+}$ ions react with $PO_4^{3-}$ and $OH^-$ ions to form a calcium phosphate which has a relatively low solubility limit in the aqueous phosphate solution. As the dissolution of the glass proceeds, the concentration of calcium phosphate increases in the solution until the solubility limit of calcium phosphate is exceeded and, as a consequence, hydroxyapatite (a form of calcium phosphate) is deposited as a porous layer on the outer surface of the dissolving glass. The formation of this porous hydroxyapatite layer on the glass surface, however, does not prevent further dissolution of the glass. Rather, the glass continues to dissolve and, as it does, the thickness of the porous hydroxyapatite layer increases. Eventually, the glass is completely reacted or transformed, leaving only a porous hydroxyapatite substance whose shape and size are the same as the initial glass fiber. Hydroxyapatite has crystallographic and chemical properties similar to those of mammalian bone. For example, human bone is a composite of fibrous protein, collagen, and hydroxyapatite.

The material for use in the invention is also selected to be of a composition which is available in fibers or which can be pulled into fibers. Glass fibers can be made several ways. For example, glass fibers can be made by pulling by hand or with use of a rotating drum directly from a melt, or they can be pulled through a bushing of a particular size. The composition is preferably selected to be of a type which softens to facilitate self-joining at a temperature below its crystallization temperature. Suitable bioactive glasses include, for example those listed in Table 1.

TABLE 1

Weight Percent Composition of Bioactive Glasses

| $Li_2O$ | $Na_2O$ | $K_2O$ | MgO | CaO | $B_2O_3$ | $P_2O_5$ | $SiO_2$ |
|---|---|---|---|---|---|---|---|
| 0 | 20 | 10 | 5 | 10 | 0 | 0 | 55 |
| 0 | 18 | 9 | 0 | 14 | 1 | 4 | 54 |
| 0 | 12 | 15 | 5 | 11 | 1 | 2 | 54 |
| 0 | 6 | 12 | 5 | 20 | 0 | 4 | 53 |
| 0 | 18 | 6 | 2 | 17 | 2 | 2 | 53 |
| 0 | 15 | 12 | 2 | 11 | 3 | 4 | 53 |
| 0 | 20 | 10 | 2 | 10 | 3 | 3 | 52 |
| 0 | 20 | 10 | 5 | 10 | 3 | 0 | 52 |
| 0 | 25 | 5 | 2 | 10 | 3 | 3 | 52 |
| 0 | 15 | 15 | 2 | 15 | 3 | 0 | 50 |
| 0 | 6 | 12 | 5 | 20 | 17.7 | 4 | 35.3 |
| 0 | 6 | 12 | 5 | 20 | 35.3 | 4 | 17.7 |
| 0 | 6 | 12 | 5 | 20 | 53 | 4 | 0 |
| 0 | 21.5 | 0 | 0 | 21.5 | 0 | 4 | 53 |
| 11.5 | 0 | 0 | 0 | 10 | 78.5 | 0 | 0 |
| 10.7 | 0 | 0 | 0 | 15 | 74.3 | 0 | 0 |
| 10 | 0 | 0 | 0 | 20 | 70 | 0 | 0 |

Glasses which crystallize under fiber-pulling conditions and/or which crystallize at a temperature below that where they soften sufficiently for joining such as 45S5 have some limited applications here but are generally avoided in the preferred embodiments because they become too brittle and weak. Bioactive glasses such as 45S5 and other glasses that crystallize quickly not allowing sufficient self-bonding to occur may be bonded with sodium silicate or some other bonding agent to form an alternative scaffold embodiment of the invention; however the strength will likely be relatively low in comparison with self-bonded scaffolds.

Figure 3A:
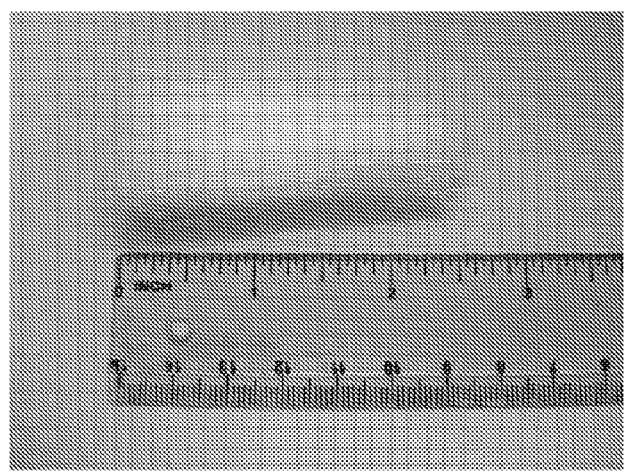
FIGS. 3A, 3B, and 3C are a series of photographs showing the manufacturing progression of a unidirectional scaffold from loose fibers to a self-bonded scaffold of the invention.
Figure 3B:
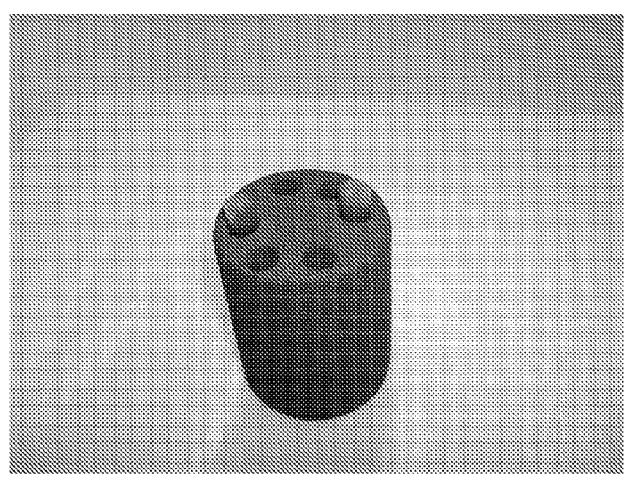

In forming the scaffold of the invention, a bundle of glass fibers such as the 6.25 cm long loose cut fibers shown in FIG. 3A is placed as shown in 3B in a mold or similar vessel which, upon softening, joining, and cooling of the glass, will impart the desired final shape and strength to the scaffold. Each of the bundles inserted as shown in FIG. 3B weighs about 2.4 grams and the mold is about 5.6 cm long. In one embodiment, this vessel is a graphite mold such as a hollowed out cylinder as shown in 3B. The fibers are placed in the vessel tightly enough to fill the vessel cavity, but not so tightly as to risk breakage of the fibers or excessive densification. The vessel is then placed in a furnace and heated at a rate of about 20° C./min in the presence of a suitable atmosphere such as air, oxygen, or nitrogen. The temperature and the heating time are selected depending on the glass composition to achieve softening and bonding of the fibers while avoiding too much bonding which would not achieve the desired porosity. The joining is preferably self-joining in that the softening of the glass accomplishes joining and no added joining agents are employed. That is, the scaffold body consists only of joined fiber elements and no other elements. As a general proposition, the vessel is heated to a temperature between about 500 and about 800° C. and held at that temperature for between about 5 and about 60 minutes. For example, in one embodiment where the scaffold is formed from type 13-93 glass fibers to a finished dimension of about 62.5 mm long and about 6 mm in diameter, the vessel is heated to a temperature between about 695 and about 705° C. and held at that temperature for between about 5 and about 45 minutes. After bonding, the vessel and scaffold are cooled, preferably in air, at a rate which avoids cracking of the bonded fibers, such as between about 10 and about 30° C. per minute.

Figure 3C:
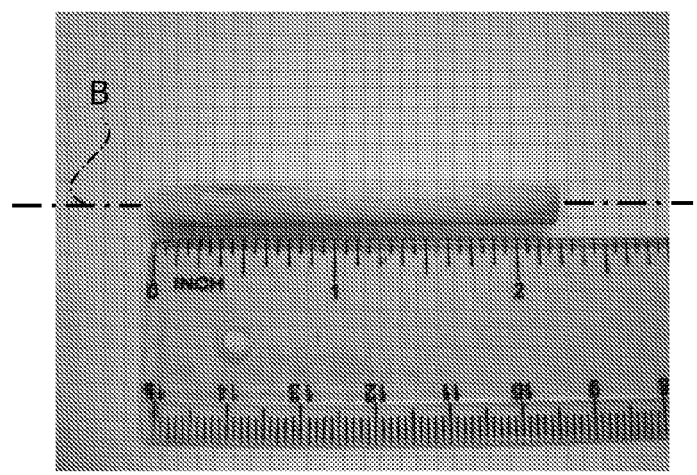

The scaffold is then removed from the vessel and cut to the desired length to yield the product shown in FIG. 3C. Cutting is accomplished, for example, by filling the pores with a wax, cutting the scaffold to length with a sharp, non-burring (e.g., diamond) saw, and then chemically or thermally removing the wax. Sharp corners and edges are avoided by making clean cuts while the scaffold is impregnated with wax, or a polish can be done with either grinding paper or a mechanical polishing device such as a Dremel tool, also done while wax impregnated.

The scaffold can be pre-reacted in a phosphate solution such as simulated body fluid (SBF) or an alkali phosphate solution to form a reacted surface layer of hydroxyapatite, prior to sterilization and implantation in a mammal. The hydroxyapatite surface layer thickness can be controlled by predetermined conversion kinetics of the glass in a phosphate containing solution. Heat treatment of the glass can induce glass crystallization which may be beneficial in the formation of glass-ceramics or ceramics. Chemical (acid) etching may add surface roughness which could be beneficial to cell attachment. Heat treating the glass to cause phase separation to form multiple phases which could react at different rates and form a new microstructure within the individual self-bonded fibers is desirable in certain applications. It is also within the scope of this invention to incorporate additives such as growth factors, medicines, etc. into the scaffold body which perform a function such as assist with tissue regrowth or supplement reinforcement of the body. In most preferred embodiments, such additives or reinforcements constitute less than about 10 vol. % of the scaffold, such that the fibers and the porosity cumulatively constitute at least about 75 vol. % of the scaffold body, for example at least about 90 vol. %. And in some embodiments there are no such additives or reinforcements, such that the scaffold body consists essentially of the fibers and the porosity.

After the wax has been removed, the scaffolds are sterilized. A preferred method among several possible is dry heat sterilization. The scaffolds are placed in a clean glass vial, covered with a clean aluminum foil cap, and heated to approximately 300° C. for three to four hours. Upon cooling, the sterile scaffolds are ready to be implanted.

Growth factors, medicines such as antibiotics, seeded cells or other biological material, liquids or gels of any type, coatings (particles, spheres, hollow spheres, thin film(s), fibers, and hollow fibers), an interpenetrating phase such as a biodegradable polymer or bone cement (PMMA) or other biological polymer, other organic or inorganic materials, or any combination may be added after sterilization to promote the growth of tissues into the scaffold. Additional sterilization may be required for scaffolds that have had inorganic non-sterile components added, and the method of sterilization may vary with the material(s) added.

In one alternative embodiment of the invention, a titanium or other biocompatible support such as a rod is incorporated into the scaffold to provide additional mechanical strength, as shown in FIGS. 10-13.

The unidirectional scaffold of the invention is suitable in one aspect for forming a complete replacement bone or tissue segment where the mammal's original bone or other tissue segment has been removed, crushed, decimated by disease or the like. In another aspect the scaffold is suitable as a bridge such as between about 2 mm and about 25 mm in length for bridging two separated bone segments. The scaffold is intended to serve as a temporary bridge for facilitating fluidic (e.g., marrow) communication (or transport) between the separated bone segments, thereby facilitating the healing of the broken bones. The scaffold also serves as an internal splint providing support for the bone fracture while the bone heals.

Example 1

Fibers of the bioactive glass type 13-93 (~2.4 grams) produced at Missouri University of Science & Technology having diameters in the range of about 50 to about 400 microns and lengths of about 62 mm were placed inside a graphite mold formed by hollowing out a graphite cylinder. The mold was then placed in a furnace (Neytech Model 2-525) and heated in air to a temperature of about 700° C., where it was held for times ranging from 5 to 45 minutes. The heat source was discontinued and the mold cooled to room temperature at an average cooling rate of about 30° C./min. Cylindrical scaffolds of unidirectional self-bonded fibers were removed from the mold, sectioned, and photographed to provide the images in FIGS. 1A, 1B, and 1C. The diameter of the scaffolds was 6 mm. FIG. 1A depicts a scaffold heated for a shorter period of time having a lower degree of self bonding, higher porosity, and lower strength. FIGS. 1B and 1C depict a scaffold heated for a longer period of time, having a greater degree of self bonding, lower porosity, and greater strength. In 1B and 1C the pore size is approaching too small, thereby inhibiting fluid flow in the scaffold in comparison to FIG. 1A. Open pores of at least about 100 microns in cross section are required for bone growth.

Example 2

Figure 4A:
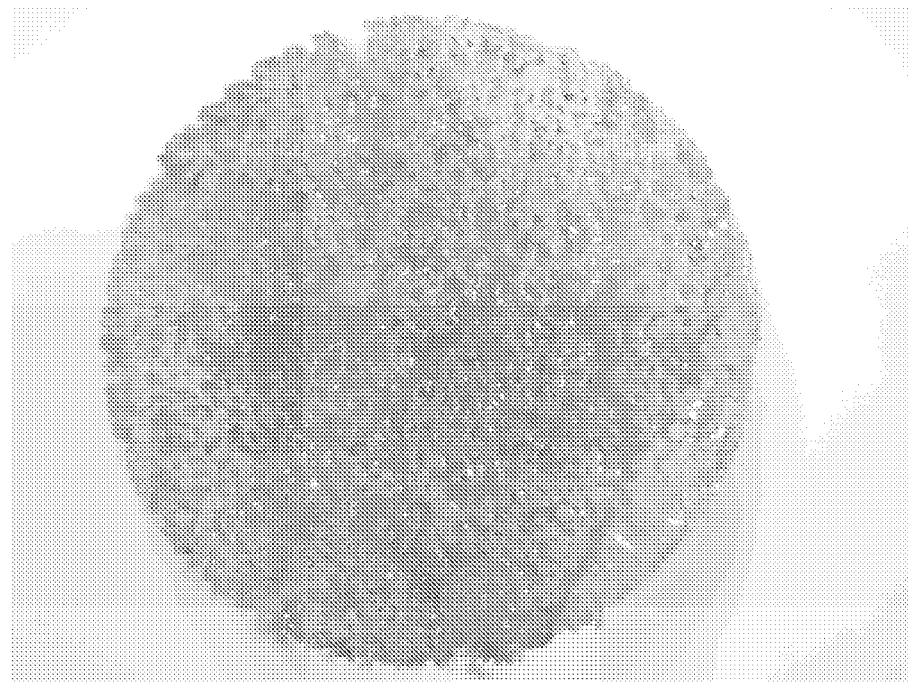
FIGS. 4A and 4B are photographs of a segment of scaffold of the invention after immersion in an osteoblast cell culture and MTT labeling.
Figure 4B:
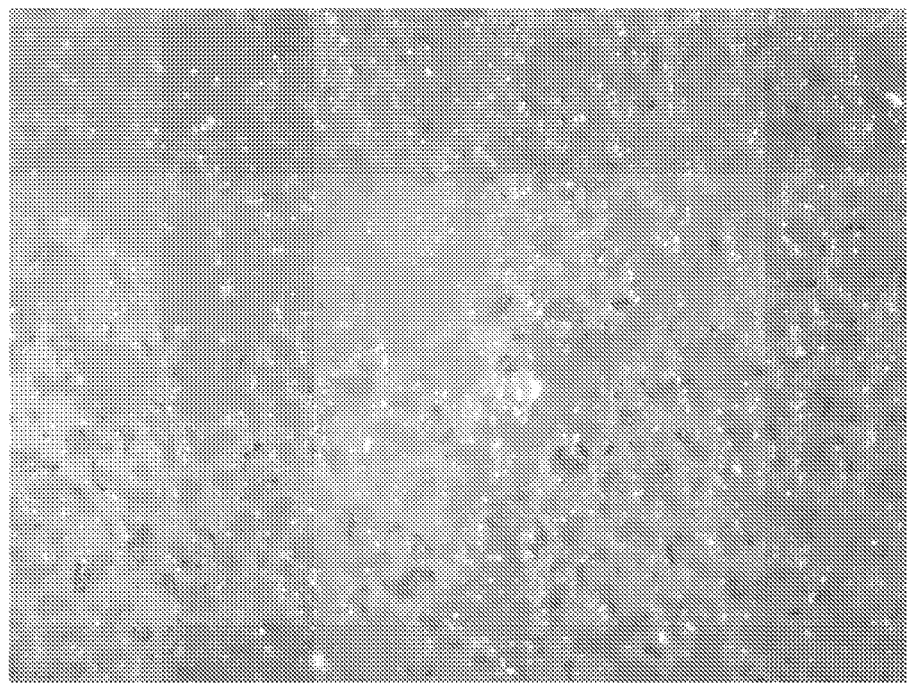

A 6 mm diameter by 20 mm thick section of a unidirectional scaffold produced according to Example 1 was placed in a culture of osteoblast cells for four hours. MTT labeling was then performed on the section and photographs were taken (FIGS. 4A and 4B). The dark spots are due to the uptake of viable osteoblast-like cells into the scaffold.

Example 3

Figure 5:
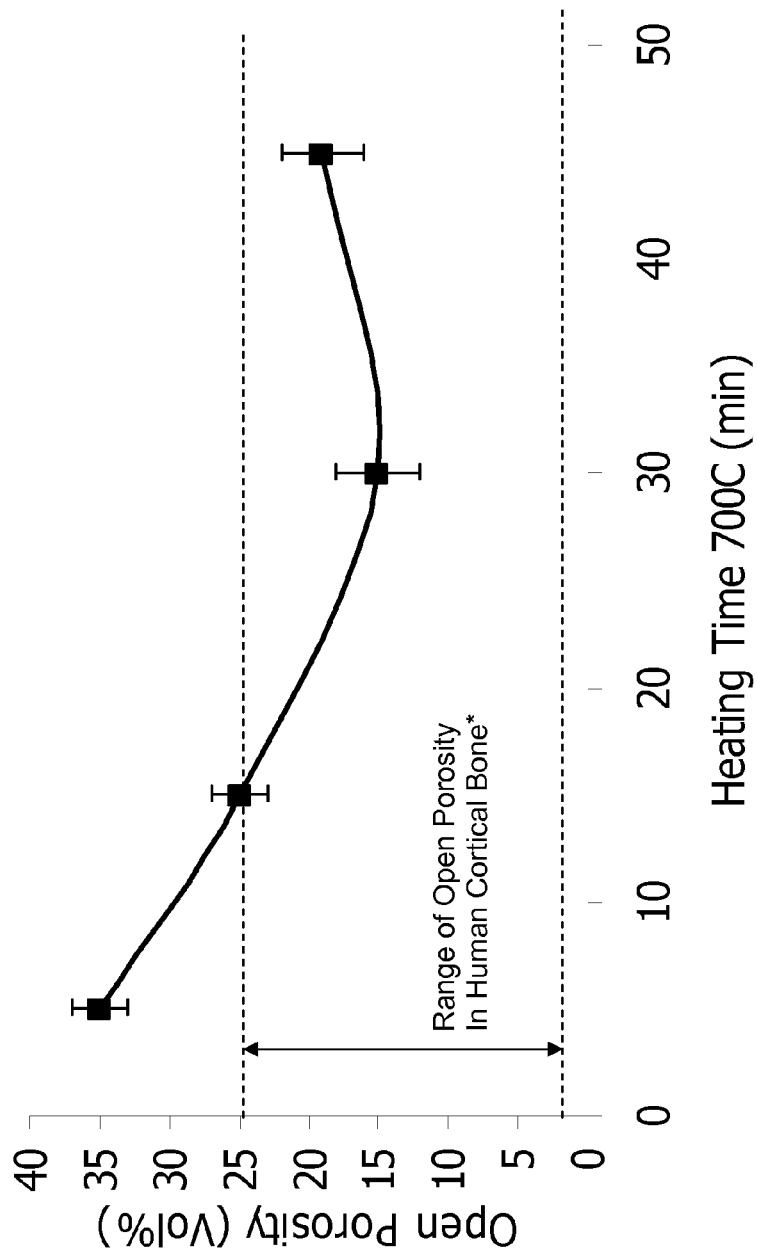
FIGS. 5 and 6 are graphical plots of open porosity and compressive strength data of scaffolds of the invention.

Unidrectional glass scaffolds were prepared in accordance with Example 1 with joining/heating times at 700° C. of 5, 15, 30, and 45 minutes. The open porosity of each scaffold was then determined by the Archimedes liquid displacement method to be 35, 25, 15, and 18 vol %, respectively; see FIG. 5. This degree of open porosity is within the range of human cortical bone and was achieved for scaffolds heated for 15, 30, and 45 minutes.

Example 4

Figure 6:
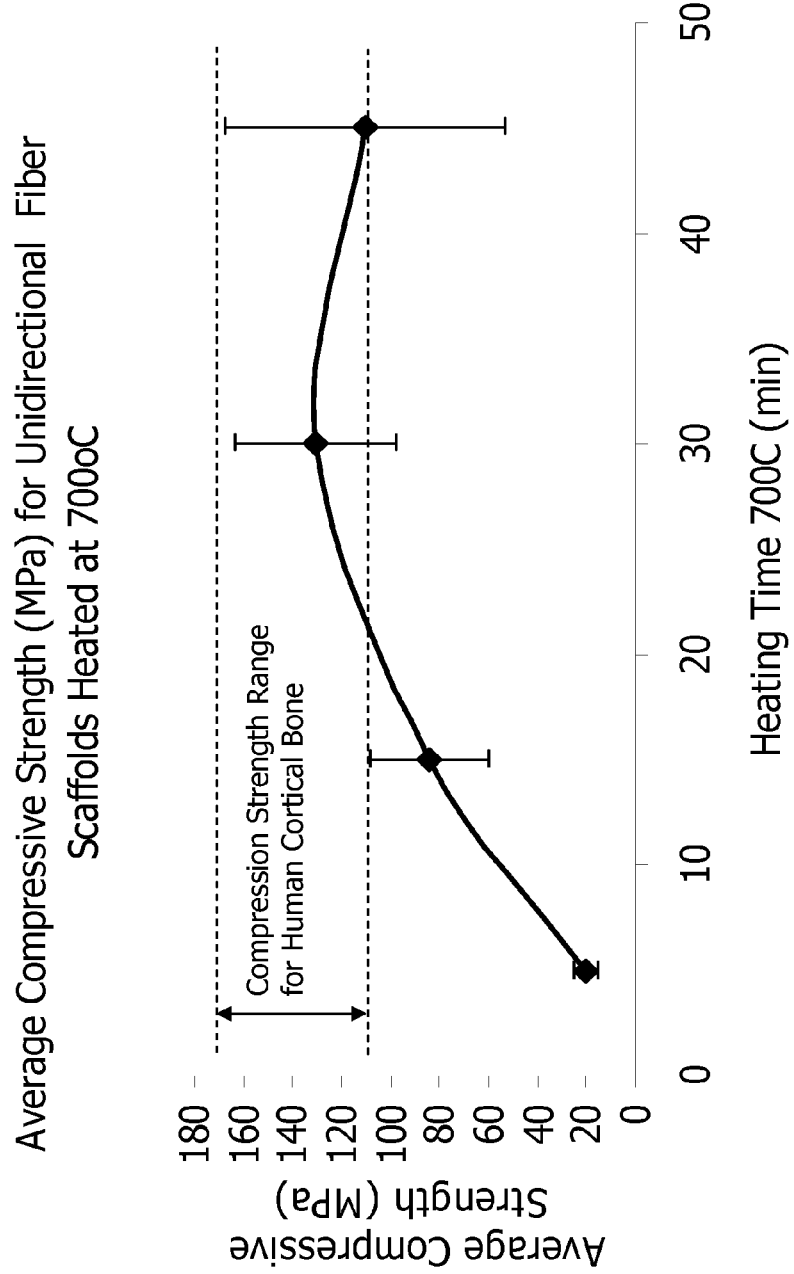

Unidirectional glass scaffolds were prepared in accordance with Example 1 with joining/heating times at 700° C. of 5, 15, 30, and 45 minutes. The average compressive strength of each scaffold was then determined by mechanical compression testing (Instron mechanical test instrument Model 4204 with a crosshead speed of 0.5 mm/min) to be 20, 80, 130, and 112 MPa, respectively, see FIG. 6. This demonstrates that compressive strengths within the range of human cortical bone were achieved for the scaffolds heated for 30 and 45 minutes.

Example 5

A unidirectional scaffold was prepared in accordance with this invention by molding, bonding, cooling, and then machining to mimic the configuration of a chicken bone. FIG. 7 shows the scaffold next to leg bone of a chicken. The scaffold of the invention, which is the lighter-colored of the two specimens closer to the ruler in FIG. 7, has a length of about 50 mm. This unidirectional scaffold is composed of fibers which were oriented parallel to the longitudinal axis of this object.

Example 6

A unidirectional cylindrical glass scaffold was prepared in accordance with Example 1 having a length of about 62 mm and a diameter of about 6 mm. The fibers were type 13-93 bioactive glass having a length of about 62 mm and diameters ranging from about 50 to about 400 microns. The fibers were oriented parallel to the longitudinal axis of the scaffold. The tip of the scaffold was dipped in a glycerol solution (34 wt % glycerol-66 wt % distilled water) as shown in FIG. 8. This solution has a viscosity of 2.5 centipoises at 25° C., which is in the average range for human blood. The purpose of this experiment was to demonstrate the strong capillary forces which this scaffold exerts upon a liquid resembling human blood.

A roughly 40 second video of the experiment was filmed, and frames at 9, 11, 15, and 22 seconds are shown in FIGS. 8A, 8B, 8C, and 8D, respectively. These frames show progressively upward darkening of the scaffold, which demonstrates rapid capillary uptake of the solution and its components into the scaffold, and that the scaffold of the invention has strong capillary uptake of fluid in the direction of the longitudinal axis of the fiber scaffold.

Example 7

A cylindrical, unidirectional glass scaffold was prepared in accordance with Example 1 having a length of about 62 mm and a diameter of about 6 mm. The fibers were type 13-93 bioactive glass fibers having a length of about 62 mm and a diameter of about 50 to 400 microns. The fibers were oriented parallel to the longitudinal axis of the scaffold.

An eyedropper was used to drop the same water-glycerol solution as described in Example 6 onto the external surface of the scaffold as shown in FIG. 9 for the purpose of demonstrating the rapid capillary action of the scaffold in a direction perpendicular to the longitudinal axis of the scaffold. The solution was dropped fairly quickly drop-by-drop onto the external surface of the scaffold until the scaffold became saturated with the solution. A video of this experiment was made over a 50 second period. Frames at 4 seconds (0 drops), 12 seconds (3 drops), 18 seconds (6 drops), and 43 seconds (19 drops) are shown in FIGS. 9A, 9B, 9C, and 9D, respectively. These frames show rapid capillary uptake of the solution and its components into the scaffold in both the lengthwise and transverse directions This experiment demonstrates the scaffold's high affinity for the liquid and that the scaffold retained most of the drops before becoming saturated. At the conclusion of this experiment most of the liquid was retained in the scaffold and very little of the solution had dripped out of the scaffold into the bowl, as shown in 9D.

Example 8

Figure 10:
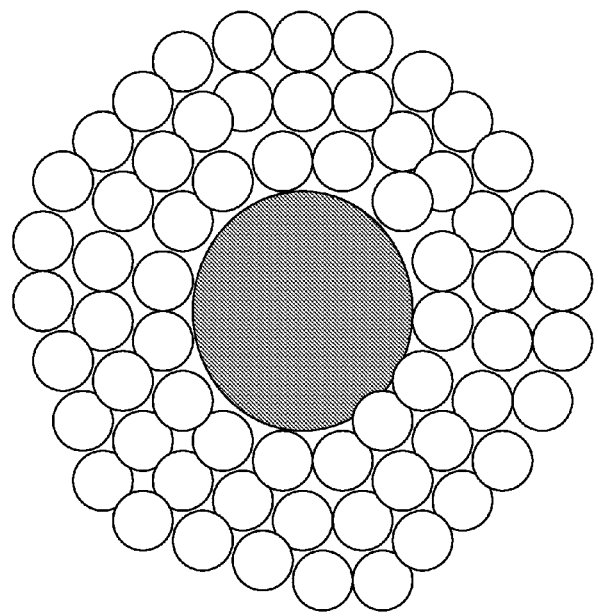
FIGS. 10, 12, and 13 are schematic depictions of alternative reinforced scaffold embodiments of the invention.
Figure 11:
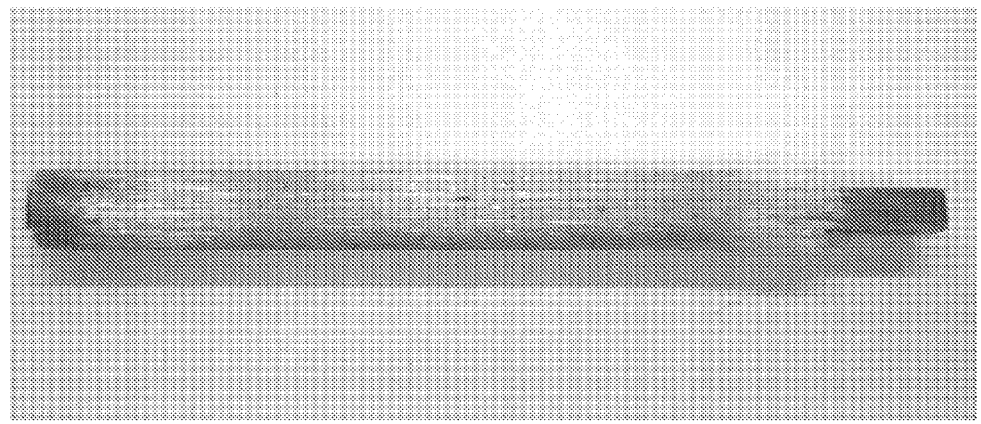
FIG. 11 is a photograph of a scaffold according to the schematic of FIG. 10.

A unidirectional scaffold was prepared generally in accordance with Example 1 having a length of about 62 mm and a diameter of about 6 mm. The fibers were type 13-93 bioactive glass fibers having a length of about 62 mm and a diameter of about 50 to 400 microns. The fibers were oriented in longitudinal co-alignment defining the length of the scaffold with an added reinforcing rod placed at the center of the fibers prior to self-bonding. FIG. 10 is a schematic pictorial demonstrating this concept of placing a reinforcement of Ti or other metal or alloy or supporting material in the center of a self-bonded unidirectional bioactive glass fiber scaffold. FIG. 11 is a photograph of the reinforced unidirectional bioactive glass scaffold prepared with a Ti rod placed in the center of a bundle of fibers, and heated so that the fibers self-bonded and also attached to the rod, in accordance with this example.

Figure 12:
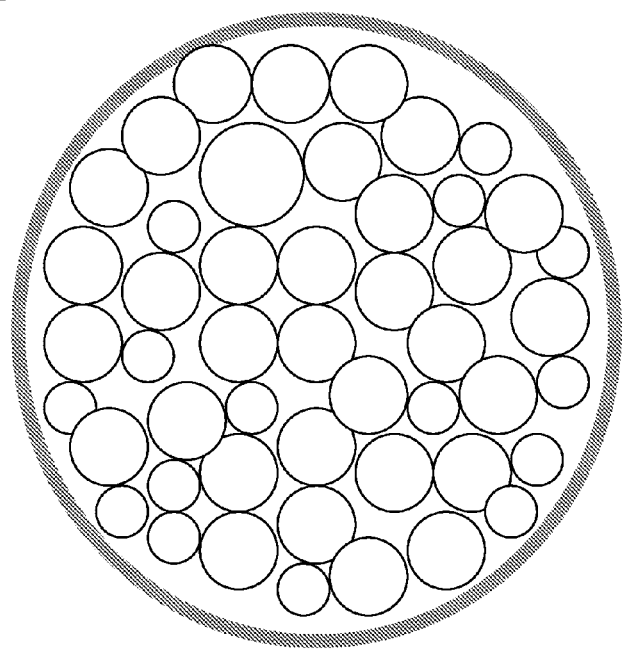

FIG. 12 is a schematic pictorial demonstrating an alternative concept of filling a hollow reinforcing tube of Ti or other metal or alloy or polymer including biodegradable polymers such as PCL or PLA or other supporting material with unidirectional glass fiber followed by self-bonding to form the scaffold. The tube is, for example, made of titanium or any other reinforcing material with similar thermal expansion properties of the glass so the scaffold bonds to the tube as the fibers self-bond. This may be beneficial in promoting bone ingrowth in prosthesis such as hip implants by inserting glass fibers into and around the implant as a means for improved bone attachment and ingrowth. FIG. 12 demonstrates an aspect of the invention, as with FIGS. 1A, 1B, and 1C, in that the fibers extending lengthwise of the scaffold central axis define channels lengthwise through a core within the scaffold. This is distinct from the alternative in FIG. 11, in which the core is occupied by a reinforcing rod rather than by channel-defining fibers.

Figure 13:
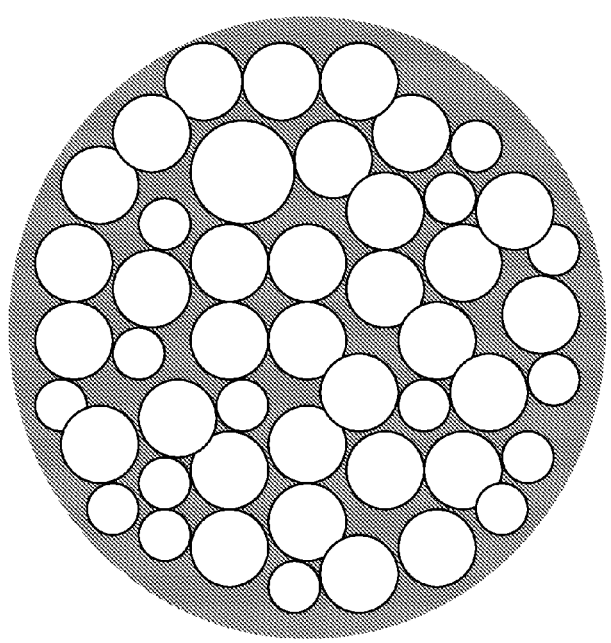

FIG. 13 is a schematic pictorial demonstrating a further alternative concept of a unidirectional bioactive glass scaffold filled with a polymer phase. Suitable polymers include those such as bone cement (PMMA) or biodegradable polymers such as PCL or PLA, as the polymer phase is used for sustained reinforcement (PMMA) or an initial reinforcement followed by a slow degradation of biodegradable polymer allowing new tissue to fill in with time. These methods associated with FIGS. 10-13 can be practiced individually or in any combination for constructing or implementing a reinforced unidirectional bioactive glass scaffold. These embodiments are distinct from the embodiments featured in FIGS. 8 and 9, where the scaffold body consists essentially of the fibers and porosity as described herein.

Example 9

Figure 14:
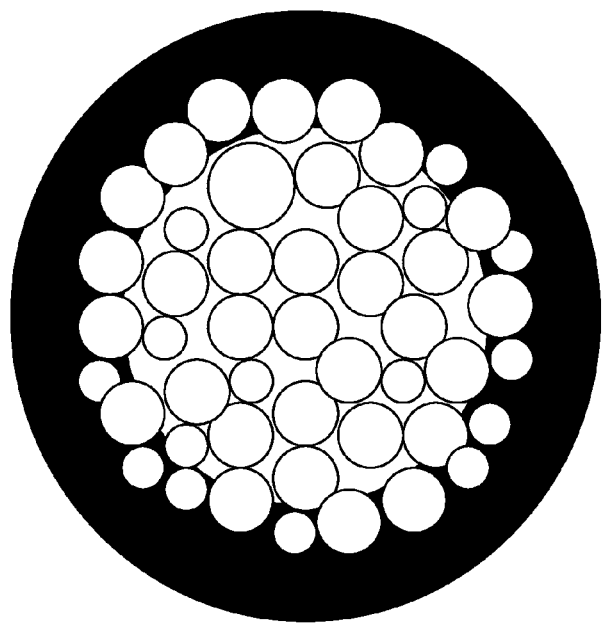
FIGS. 14, 16, 18, 19 and 21 are a schematic end view depictions of alternative scaffold embodiments.
Figure 15:
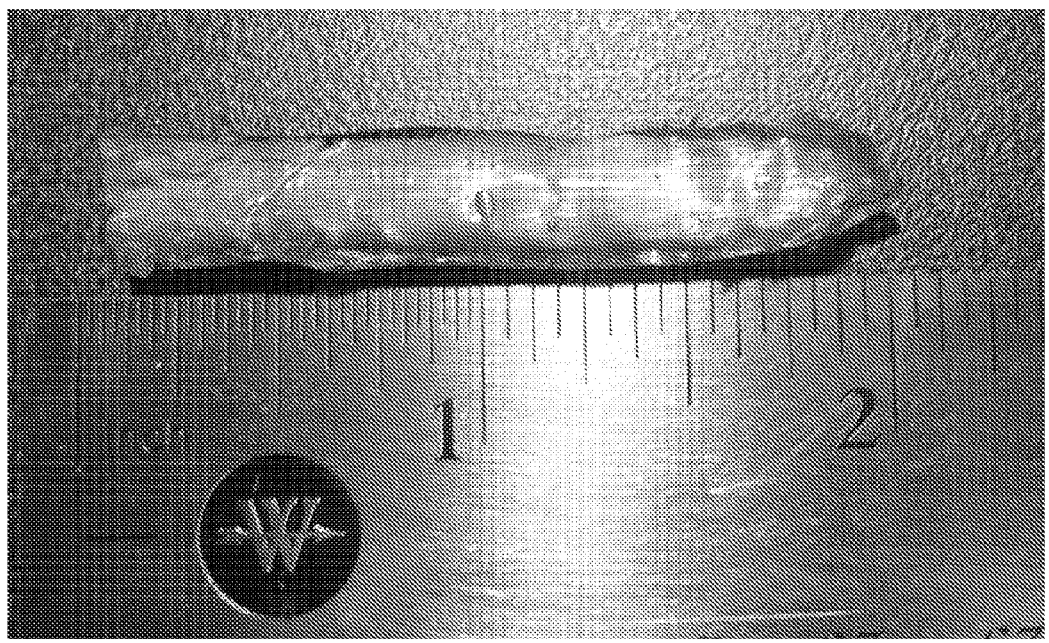
FIGS. 15, 17, and 20 are photographs of alternative scaffold embodiments.

FIG. 14 is a schematic illustration of an alternative embodiment of the invention in which biocompatible glass fibers longitudinally aligned in accordance with the invention are bonded together by dipping into a molten polymer to form a rigid outer layer, depicted as black in the figure. FIG. 15 is a photograph of a scaffold prepared this way by dipping a bundle of type 13-93 fibers into molten polymer of 82 parts polylactic acid (PLA) and 18 parts polyglycolic acid (PGA) at 250° C. The degradation rate can be controlled by selecting a mix of biocompatible polymers in proportions to impart the desired degradation. In this embodiment and other embodiments, it is also possible to spray or otherwise coat the individual fibers with a polymer such as PLA or PGA which affects degradation.

Example 10

Figure 16:
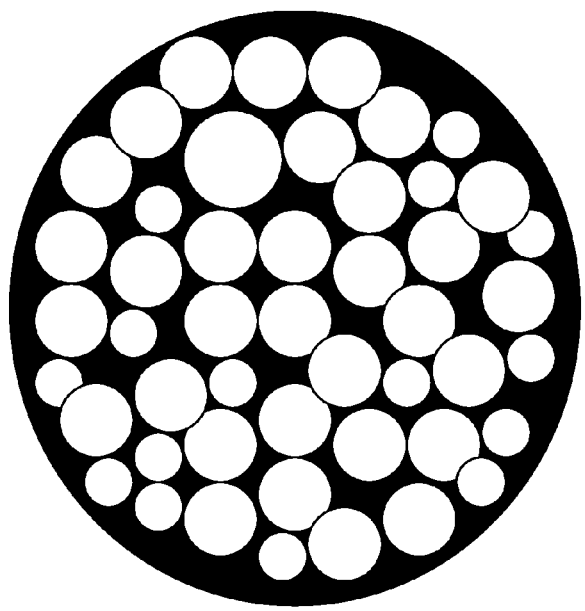
Figure 17:
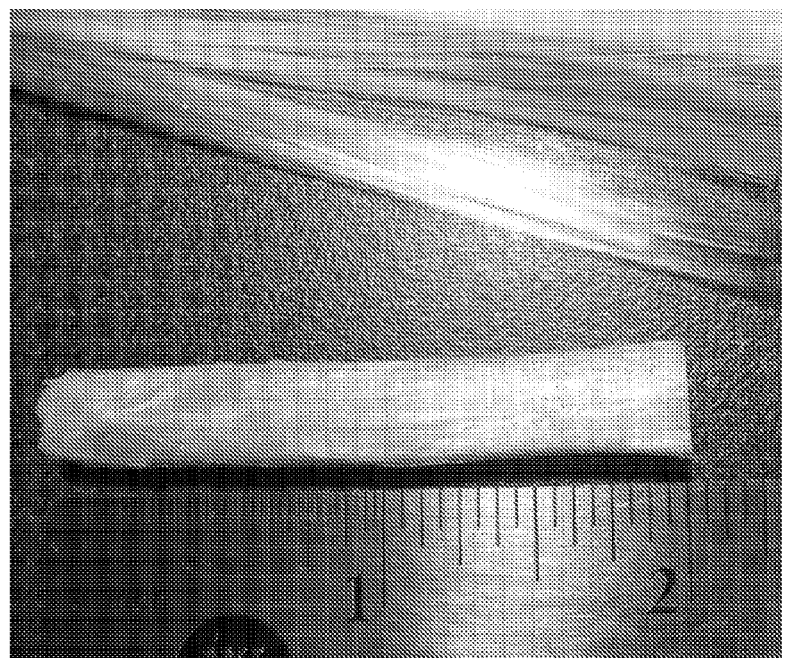

FIG. 16 is a schematic illustration of an alternative embodiment of the invention in which biocompatible glass fibers longitudinally aligned in accordance with the invention are bonded together by dipping into a bath of a polymer dissolved in a solvent. By dissolving the polymer in a solvent, the polymer depicted here in black is able to flow into the interior of the bundle of fibers, in contrast to the embodiment in FIG. 14. FIG. 17 is a photograph of a scaffold prepared this way by dipping a bundle of type 13-93 fibers into a polymer of 82 parts polylactic acid (PLA) and 18 parts polyglycolic acid (PGA) dissolved in a solvent.

Example 11

Figure 18:
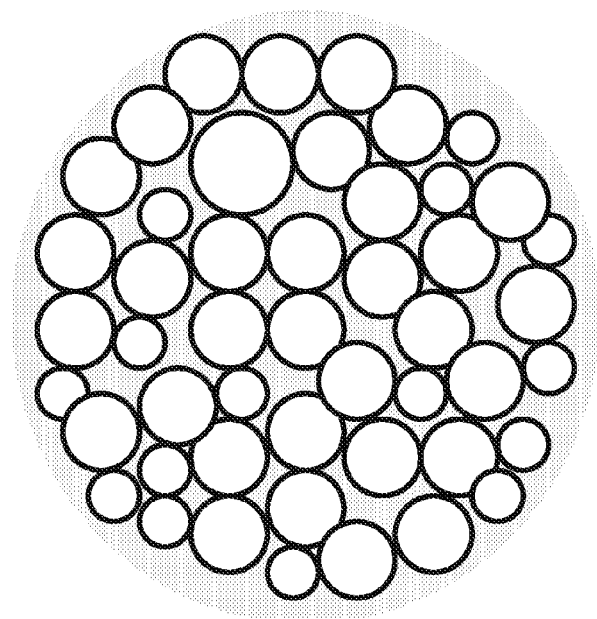
Figure 19:
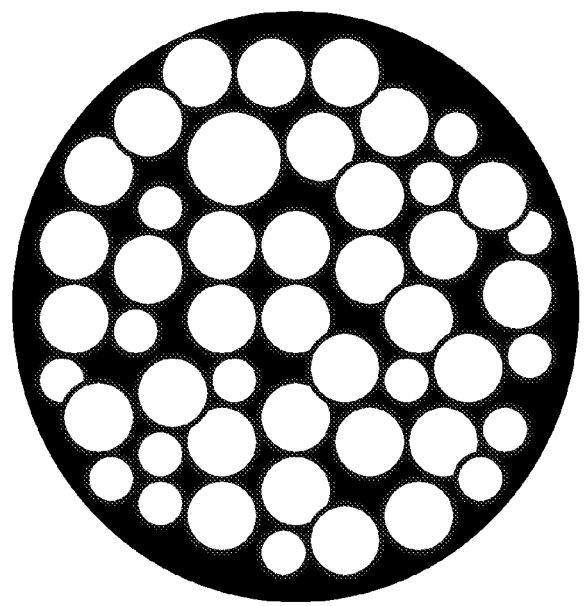
Figure 20:
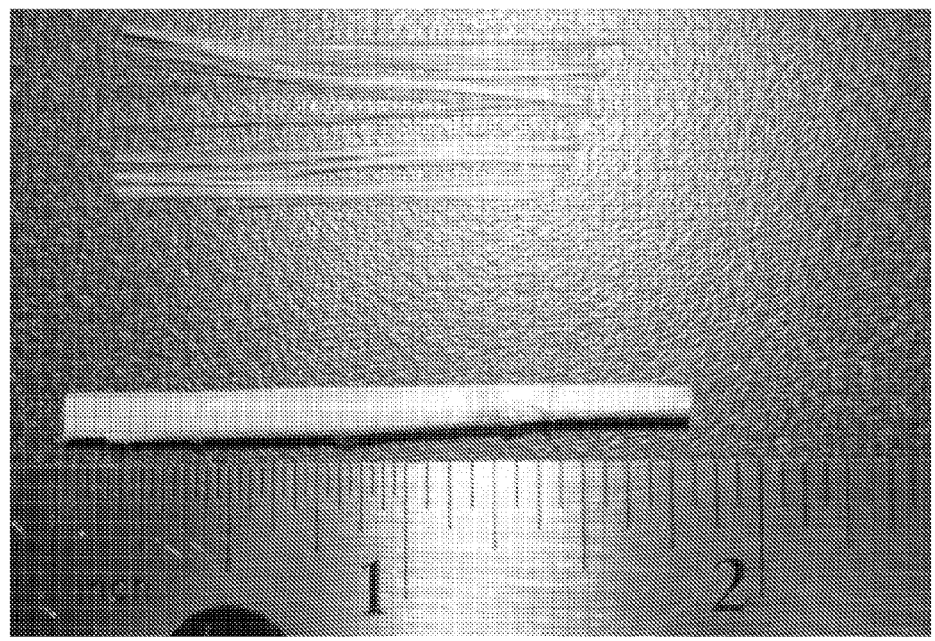

FIG. 18 is a schematic illustration of a further alternative embodiment of the invention in which biocompatible glass fibers longitudinally aligned in accordance with the invention are precoated with PLA, then bonded together as shown in FIG. 19. FIG. 20 is a photograph of a scaffold prepared this way by dipping a bundle of type 13-93 fibers into an 82:18 mixture of PLA/PGA in a solvent. In this embodiment, the thickness of the polymer coating is, for example, at least about 500 nm, such as between about 0.5 micron and about 10 microns, or between about 1 micron and about 5 microns.

Figure 21:
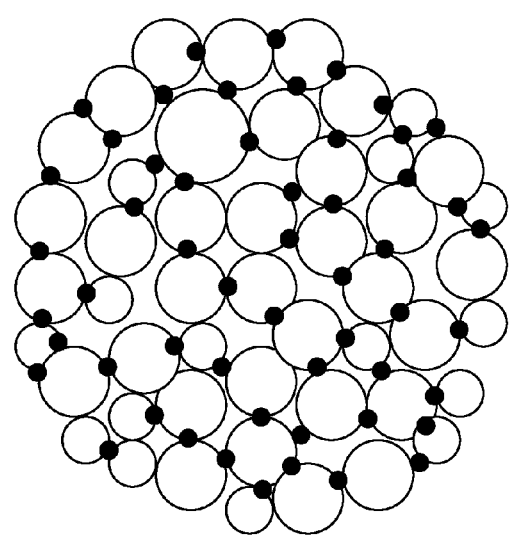

It can be seen from FIGS. 14-20, therefore, that the rigidity required in the invention can be imparted by bonding the longitudinally aligned fibers to each other by polymer bonding. As further alternatives, the precoated longitudinally aligned fibers shown in FIG. 18 can be bonded to each other by exposing the polymer coating to a solvent to partially dissolve the coating. Then adjacent fibers bond to each other as the polymer re-solidifies upon removal of the solvent. Or the polymer coating on the fibers can be softened by heating, then hardened by cooling, leaving adjacent fibers bonded to each other. A still further alternative is to dust the fibers with polymer such that the polymer is more occasional and intermittent as shown in FIG. 21, in contrast to the continuous polymer coating shown in FIG. 18. Then the scaffold can be heated to soften the polymer such that it will bond the adjacent longitudinally aligned fibers at various points.

Among the polymer materials suitable for the polymer tube shown in FIG. 12, the polymer fill in FIG. 13, the polymer dip coating in FIG. 14, and the polymer coating on fibers in FIG. 18 are, for example, polycaprolactones (PCL), poly-L-Lactic acid (PL-LA), polyvinyl alcohol (PVA), polyglycolic acid (PGA), polyacrylic acids (PAA), poly ethylene glycol (PEG), poly-L-Lactic gylcolic acid (PLGA), polyesters, polyalkenoics, polyolefins, polysulfones, poly (anhydrides), poly(hydroy acids), polyglycolides, polylactides, poly(propylene fumerates), polyacetals, polycarbonates, polyamino acids, poly)orthoesters), polyamides, poly (vinyl pryyolidones), poly(dioxanones), polyhydroxyvalyrates, polyhydroxybutyrates, biodegradable polycyanoacrylates, biodegradable polyurethanes, poly (methyl vinyl ether), poly(esteramides), polyketals, poly (glyconates), poly(maleic anhydride), poly(maleic acid), poly(alkylenesuccinates), poly(ppyrrole), polyphosphazines, poly(maleic anhydride), tyrosine-based polymers, polysaccharides, poly(alkylene oxalates), poly(orthocarbonates), poly(ethylene oxide), polyureas, poly(ethylene vinyl acetate), polystyrene, polypropylene, polymethacrylate, polyethylene, poly(aniline), poly(thiophene), non-biodegradable polyurethanes, co-polymers, adducts, and mixtures thereof.

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A tissue scaffold for repair and regeneration of bone hard tissue or muscle, skin, or organ soft tissue, the scaffold comprising:
   a rigid scaffold body having a scaffold central axis, a scaffold transverse dimension, and a scaffold lengthwise dimension which is greater than the scaffold transverse dimension, the scaffold body having a compressive strength between about 20 and about 250 MPa and comprising:
   biocompatible inorganic glass fibers each having a fiber transverse dimension and a fiber lengthwise dimension which is at least about 10 times the fiber transverse dimension; and
   wherein each of the fibers has a diameter between about 20 and about 5000 microns;
   wherein at least about 75 vol % of the fibers are longitudinally co-aligned and lie generally lengthwise of the scaffold central axis, are generally free of helical orientation about the scaffold central axis, and are arranged to define open channels within the scaffold which allow fluid flow into and lengthwise within the scaffold; and
   wherein adjacent longitudinally co-aligned fibers are bonded together.

2. The tissue scaffold of claim 1 wherein each fiber among the at least about 75 vol % of fibers has an alignment along at least about 75% of its length which does not deviate more than about 25 degrees from parallel to the central axis of the scaffold.

3. The tissue scaffold of claim 1 wherein each fiber among the at least about 75 vol % of fibers is generally straight.

4. The tissue scaffold of claim 1 wherein the scaffold body has an interconnected porosity.

5. The tissue scaffold of claim 4 wherein the fibers and the porosity cumulatively constitute at least about 75 vol. % of the scaffold body.

6. The tissue scaffold of claim 4 wherein the scaffold body consists essentially of the glass fibers and the porosity.

7. The tissue scaffold of claim 1 wherein the scaffold body has an interconnected porosity between about 10 vol. % and about 35 vol. % of the scaffold body.

8. The tissue scaffold of claim 5 wherein the scaffold body consists essentially of the glass fibers and the porosity.

9. The tissue scaffold of claim 1 wherein the fibers are bioactive glass fibers.

10. The tissue scaffold of claim 1 wherein the fibers are self-bonded together in that adjacent longitudinally aligned fibers are fused together.

11. The tissue scaffold of claim 1 wherein the scaffold body of fibers is filled with a polymer phase.

12. The tissue scaffold of claim 11 wherein the polymer phase comprises PMMA, PCL, or PLA.

13. The tissue scaffold of claim 11 wherein the polymer phase is a polymer selected from the group consisting of polycaprolactones (PCL), poly-L-Lactic acid (PL-LA), polyvinyl alcohol (PVA), polyglycolic acid (PGA), polyacrylic acids (PAA), poly ethylene glycol (PEG), poly-L-Lactic gylcolic acid (PLGA), polyesters, polyalkenoics, polyolefins, polysulfones, poly(anhydrides), poly(hydroy acids), polyglycolides, polylactides, poly(propylene fumerates), polyacetals, polycarbonates, polyamino acids, poly) orthoesters), polyamides, poly(vinyl pryyolidones), poly(dioxanones), polyhydroxyvalyrates, polyhydroxybutyrates, biodegradable polycyanoacrylates, biodegradable polyurethanes, poly(methyl vinyl ether), poly(esteramides), polyketals, poly(glyconates), poly(maleic anhydride), poly (maleic acid), poly (alkylene succinates), poly(ppyrrole), polyphosphazines, poly(maleic anhydride), tyrosine-based polymers, polysaccharides, poly(alkylene oxalates), poly (orthocarbonates), poly(ethylene oxide), polyureas, poly (ethylene vinyl acetate), polystyrene, polypropylene, polymethacrylate, polyethylene, poly(aniline), poly(thiophene), non-biodegradable polyurethanes, co-polymers, adducts, and mixtures thereof.

14. The tissue scaffold of claim 1 wherein the rigid scaffold body further comprises a reinforcing tube of biodegradable polymer with the biocompatible inorganic glass fibers within the tube.

15. The tissue scaffold of claim 14 wherein the biodegradable polymer comprises PCL or PLA.

16. The tissue scaffold of claim 15 wherein the biodegradable polymer is selected from the group consisting of polycaprolactones (PCL), poly-L-Lactic acid (PL-LA), polyvinyl alcohol (PVA), polyglycolic acid (PGA), polyacrylic acids (PAA), poly ethylene glycol (PEG), poly-L-Lactic gylcolic acid (PLGA), polyesters, polyalkenoics, polyolefins, polysulfones, poly(anhydrides), poly(hydroy acids), polyglycolides, polylactides, poly(propylene fumerates), polyacetals, polycarbonates, polyamino acids, poly) orthoesters), polyamides, poly(vinyl pryyolidones), poly(dioxanones), polyhydroxyvalyrates, polyhydroxybutyrates, biodegradable polycyanoacrylates, biodegradable polyurethanes, poly(methyl vinyl ether), poly(esteramides), polyketals, poly(glyconates), poly(maleic anhydride), poly (maleic acid), poly (alkylene succinates), poly(ppyrrole), polyphosphazines, poly(maleic anhydride), tyrosine-based polymers, polysaccharides, poly(alkylene oxalates), poly (orthocarbonates), poly(ethylene oxide), polyureas, poly (ethylene vinyl acetate), polystyrene, polypropylene, polymethacrylate, polyethylene, poly(aniline), poly(thiophene), non-biodegradable polyurethanes, co-polymers, adducts, and mixtures thereof.

17. The scaffold of claim 1 wherein adjacent longitudinally co-aligned fibers are bonded together by adhesive or by fusing at a temperature at which the fibers soften and self-bond to each other.

18. The tissue scaffold of claim 17 wherein the adjacent longitudinally co-aligned fibers are bonded together by the adhesive, the adhesive is a polymer, and the adjacent longitudinally co-aligned fibers are bonded together by polymer bonding.

19. The tissue scaffold of claim 18 wherein the adjacent longitudinally co-aligned fibers have a coating of said polymer thereon.

20. The tissue scaffold of claim 19 wherein the polymer coating comprises polymer selected from the group consisting of PLA, PGA, and mixtures thereof.

21. The tissue scaffold of claim 19 wherein the polymer coating comprises polymer selected from the group consisting of polycaprolactones (PCL), poly-L-Lactic acid (PLLA), polyvinyl alcohol (PVA), polyglycolic acid (PGA), polyacrylic acids (PAA), poly ethylene glycol (PEG), poly-L-Lactic gylcolic acid (PLGA), polyesters, polyalkenoics, polyolefins, polysulfones, poly(anhydrides), poly(hydroy acids), polyglycolides, polylactides, poly(propylene fumerates), polyacetals, polycarbonates, polyamino acids, poly) orthoesters), polyamides, poly(vinyl pryyolidones), poly(dioxanones), polyhydroxyvalyrates, polyhydroxybutyrates, biodegradable polycyanoacrylates, biodegradable polyurethanes, poly(methyl vinyl ether), poly(esteramides), polyketals, poly(glyconates), poly(maleic anhydride), poly (maleic acid), poly (alkylene succinates), poly(ppyrrole), polyphosphazines, poly(maleic anhydride), tyrosine-based polymers, polysaccharides, poly(alkylene oxalates), poly (orthocarbonates), poly(ethylene oxide), polyureas, poly (ethylene vinyl acetate), polystyrene, polypropylene, polymethacrylate, polyethylene, poly(aniline), poly(thiophene), non-biodegradable polyurethanes, co-polymers, adducts, and mixtures thereof.

22. The scaffold of claim 19 wherein the bonding is achieved by dissolving and re-solidifying the polymer coating.

23. The scaffold of claim 19 wherein the bonding is achieved by softening by heating then hardening by cooling the polymer coating.

24. The scaffold of claim 17 wherein the adjacent longitudinally co-aligned fibers are bonded together by the adhesive and the adhesive comprises an intermittent polymer coating on the fibers.

25. The scaffold of claim 1 wherein each of the fibers has a diameter between about 50 and about 400 microns.

26. The scaffold of claim 1 wherein each of the fibers has a diameter between about 100 and about 450 microns.

* * * * *